United States Patent [19]

Brunavs et al.

[11] Patent Number: 5,378,717
[45] Date of Patent: Jan. 3, 1995

[54] THERAPY FOR DIABETIC COMPLICATIONS

[75] Inventors: Michael Brunavs, Frimley; Colin P. Dell, Dorking; Peter T. Gallagher, Camberley; William M. Owton, Lightwater; Colin W. Smith, Bracknell, all of England

[73] Assignee: Eli Lilly and Company, Indianapolis, Ind.

[21] Appl. No.: 34,059

[22] Filed: Mar. 22, 1993

Related U.S. Application Data

[63] Continuation-in-part of Ser. No. 14,016, Feb. 5, 1993.

[51] Int. Cl.[6] .................. A61K 31/35; A61K 31/38; A61K 31/40; A61K 31/44
[52] U.S. Cl. .................. 514/337; 514/427; 514/454; 514/455; 514/444
[58] Field of Search ............. 514/454, 337, 429, 444, 514/461, 455, 427

[56] References Cited

PUBLICATIONS

Elnagdi, et al., *Naturfoschung B*, 47(4), pp. 572–578 (1992).
Elagamey, et al. *Indian Journal of Chemistry*, 29B, 885–886 (1990).
Elagamey, et al., *Collection Czechoslovak Chem. Commun.*, 53(7), 1534–1538 (1988).
Otto, et al., *Monatshefte fur Chemi*, 110, 115–119 (1979).
Otto, et al., *Monatshefte fur Chemi*, 110, 249–256 (1979).
Otto et al., *Arch. Pharm.*, 312(6), 548–550 (1979).
Maybridge Chemical Company, Structure List No. 183, May 1989.
Maybridge Chemical Company, Exclusive Listing No. 1187/513684/13279, Nov. 6, 1987.
Maybridge Chemical Company, Exclusive Listing No. 288/513845/13684, Feb. 19, 1988.

*Primary Examiner*—Marianne M. Cintins
*Assistant Examiner*—Phyllis G. Spivack
*Attorney, Agent, or Firm*—Steven P. Caltrider; David E. Boone

[57] ABSTRACT

This invention provides a method of treating diabetic complications in mammals which comprises the administration of a compound of the Formula I:

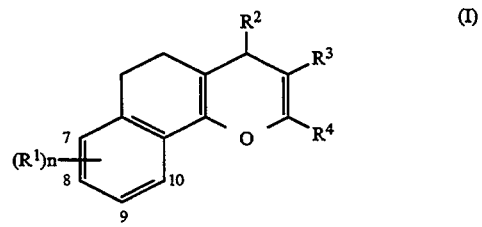

in which n, $R^1$, $R^2$, $R^3$, and $R^4$ are variables.

10 Claims, No Drawings

THERAPY FOR DIABETIC COMPLICATIONS

This application is a continuation in part of Brunavs, et al., U.S. Ser. No. 08/014,016, Pharmaceutical Compounds filed Feb. 5, 1993.

BACKGROUND OF THE INVENTION

Diabetic complications, including diabetic retinopathy, nephropathy, and neuropathy are largely the result of abnormalities in microvascular function. Changes in vascular function include increased blood vessel permeability and altered blood flow. These changes precede the development of the clinical symptoms of diabetic complications.

Diabetic retinopathy and proliferative vitreoretinopathy are characterized by the growth of new blood vessels, or anglogenesis. One of the early events in angiogenesis is secretion of proteases involved in the dissolution of the basement membrane. These proteases include the plasminogen activators, procollagenase and prostromelysin. Plasminogen activators such as urokinase (uPA) and tissue plasminogen activator (tPA) are serine proteases which cleave the zymogen plasminogen to generate the active serine protease plasmin. Plasmin can influence basement membrane integrity directly through cleavage of basement membrane components or indirectly through cleavage of procollagenase and prostromelysin to generate active collagenase and stromelysin. The resulting dissolution of the basement membrane allows the endothelial cells to escape from the microvessel and begin the neovascularization process Increased plasmin formation also has several ramifications in terms of the permeability of the diabetic microvessel. Plasmin can directly degrade basement membrane components or can activate stromelysin, thus directly or indirectly influencing the normal turnover of heparan sulfate proteoglycan (HSPG). Because HSPG is involved in blood vessel permeability as well as growth control, this enhanced degradation of HSPG may result in its depletion from the membrane with resultant increased vessel permeability.

Microvascular dysfunctions arise through this abnormal activation of endethelial cells which is mediated, in part, through protein kinase C (PKC)-regulated pathways. See MacGregor, et al., *J Clin Invest*, 83: 90-94 (1988); Lee, et al., *Proc. Natl. Acad. Sci.*, 86: 5141-5145 (1989).

Agents that block or reverse the activation of endothelial cells and inhibit the alterations in microvessel function will have a beneficial effect in terms of preserving normal structure and function in the tissues affected by the complications of diabetes. The agents will improve the quality of life and longevity of diabetics.

The present invention discloses a method of inhibiting endothelial cell activation. Accordingly, the present invention provides a method of treating diabetic complications in mammals which comprises the administration of a compound of the Formula I:

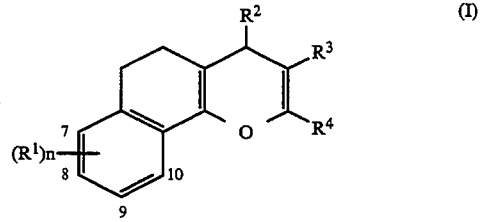

This invention covers the use of these compounds in the treatment of diabetic complications, as well as in other disease states in which there is vascular dysfunction.

SUMMARY OF THE INVENTION

This invention provides a method of treating diabetic complications in mammals which comprises the administration to a patient in need of treatment a therapeutic dosage of a compound of the Formula I:

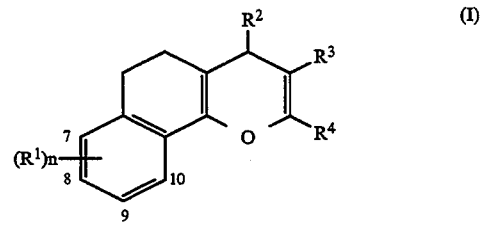

wherein n is 0, 1 or 2;

$R^1$ is $C_1$-$C_4$ alkoxy, OH, or COOH attached at any of the positions 7, 8, 9, or 10;

$R^2$ is phenyl, naphthyl or heteroaryl selected from thienyl, pyrrolyl, pyridyl, benzothienyl; said phenyl, naphthyl and heteroaryl groups being optionally substituted, or $R^2$ is furanyl optionally substituted with $C_{1-4}$ alkyl;

$R^3$ is nitrile; and $R^4$ is $-NR^{11}R^{12}$, $-NR^{11}COR^{12}$, or $-N=CHOCH_2R^{11}$ where $R^{11}$ and $R^{12}$ are each hydrogen or $C_{1-4}$ alkyl.

DETAILED DESCRIPTION AND PREFERRED EMBODIMENT

The synthesis of certain phenyl-substituted 5,6-dihydronaphtho [1,2-b] pyrans is described by Otto H-H. et al. in Monatshefte für Chemie 110, 115-119 and 249-256 (1979), and Arch. Pharm. (Weinheim Ger.), 312(6), 548-550 (1979). No biological properties are ascribed to the compounds disclosed.

In the above formula (I), a substituted phenyl group is phenyl substituted in position 3, 4, or 5 with one or two substituents. One substituent being selected from halo, $C_{1-4}$ alkoxy, nitro, or when the substitution is in position 3, trifluoromethyl, carboxy, trifluoromethoxy or $-COOR^{15}$ where $R^{15}$ is an ester group. The second substituent being selected from halo, $C_{1-4}$ alkoxy, $C_{1-4}$ alkyl, hydroxy and trifluoromethyl. In addition, substituted phenyl includes a phenyl group in which neighboring atoms are substituted by $-O(CH_2)_mO-$, where m is 1, 2 or 3.

Substituted heteroaryl groups are a heteroaryl substituted with one substituent selected from halo, $C_{1-4}$ alkyl, $C_1$-$C_4$ alkoxy, hydroxy, or trifluoromethyl.

Halo is, for example, fluoro, chloro or bromo and is especially chloro. A $C_{1-4}$ alkyl group includes, for example, methyl, ethyl, propyl and butyl, and is preferably methyl or ethyl. A $C_{1-4}$ alkoxy group is one such alkyl group linked through oxygen to an aryl nucleus.

When n is 1 or 2 and there are one or two substituents on the dihydronaphtho nucleus they can be at any of the positions 7, 9, or 10. It is preferred that the dihydronaphtho nucleus is unsubstituted or that it bears a single substituent at the 9-position.

When $R^2$ is heteroaryl, it is preferably 2-thienyl, 3-thienyl, 2-pyrrolyl, 2-pyridyl, 3-pyridyl, 4-pyridyl, 2-benzothienyl, 3-benzothienyl, 2-furanyl or 3-furanyl. A naphthyl group is attached at the 1- or 2-position. Such groups can be substituted at any of the available positions, but are preferably unsubstituted. Preferred values of $R^2$ are 2-furanyl, phenyl or substituted phenyl.

A particularly preferred value of $R^2$ is substituted phenyl, preferably phenyl with a single substituent, especially nitro or halo.

The group $R^4$ is preferably $-NR^{11}R^{12}$, where $R^{11}$ and $R^{12}$ are each hydrogen.

The group $R^{15}$ is preferably the methyl or ethyl esters.

It will be appreciated that when, for example $R^2$ is $-COOH$, an opportunity exists for salts to be formed. They can be derived from any of the well known bases. Examples of base salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such sales include ammonium hydroxide, potassium carbonate, sodium bicarbonate, lithium hydroxide, calcium hydroxide, methylamine, diethylamine, ethylene diamine, cyclohexylamine and ethanolamine. The potassium, sodium and lithium salt forms are particularly preferred.

In addition to pharmaceutically-acceptable sales, other salts are included in the invention. They may serve as intermediates in the purification of compounds or in the preparation of other, for example pharmaceutically-acceptable, acid addition salts, or are useful for identification, characterization or purification.

It will be appreciated that the compounds of the invention contain an asymmetric carbon atom which gives rise to enantiomers. The compounds are normally prepared as racemates and can conveniently be used as such, but individual enantiomers can be, isolated by conventional techniques if so desired. Such racemates and individual enantiomers form part of the present invention.

The compounds disclosed in the present invention may be prepared as follows:

(1) reacting a compound of the formula (III):

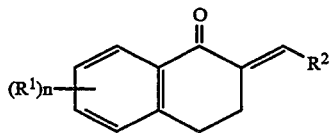

with malononitrile to give a compound of formula (I) in which $R^3$ is nitrile and $R^4$ is $-NH_2$, (2) converting a compound of the formula (IV):

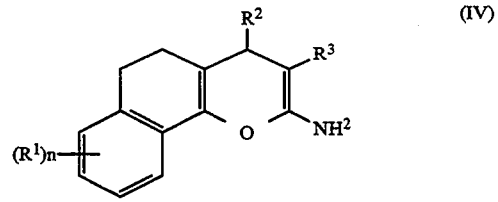

to a compound of formula (I) in which $R^4$ is $-NR^{11}R^{12}$, $-NR^{11}COR^{12}$, With regard to process (1), the reaction is preferably carried out at a temperature of from 0° C. to 100° C. and in the presence of an organic solvent, such as for example ethanol. Compounds of formula (III) are known or can be easily synthesised by known methods. For example, they can be prepared from compounds of formula:

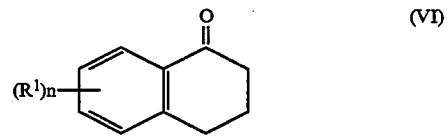

by reaction with an aldehyde of formula $R^2CHO$ in the presence of an acid catalyst such as, for example, toluene sulphonic acid, or when $R^2$ is an acid sensitive group such as pyridyl, under basic conditions, with, for example, potassium hydroxide and ethanol.

With regard to process (2), the free enamine can be prepared by reaction (1) and subsequently converted to compounds in which $R^4$ takes other values. For example, the free amino group can be alkylated with reagents of formula $R^{11}X$ or $R^{12}X$ where X is halogen, to give the mono- or di-alkylated product. Similarly the amino group can be acylazed with an acylating reagent of formula $R^{11}COX$ or $(R^{11}CO)_2O$ to give compounds in which $R^4$ is $-NR^{11}COR^{12}$. Compounds in which $R^4$ is $-N=CHOCH_2R^{11}$ are prepared by reaction with the appropriate trialkyl orthoformate.

The preparation of representative compounds of the present invention is illustrated by the following Examples.

EXAMPLE 1

Preparation of Intermediates (1) A mixture of 3,4-dihydro-1(2H)-naphthalenone (21.9 g), 3-nitrobenzaldehyde (22.6 g) and p-toluenesulphonic acid monohydrate (50 mg) in toluene (250 ml) was stirred at reflux with separation of water for 4.5 hours. The brown solution was allowed to cool overnight. The resulting yellow-orange deposited solid was filtered off, washed well with toluene and dried in vacuo yielding 2-(3-nitrobenzylidene)-3,4-dihydro-1(2H)-naphthalenone as crisp yellow needles.

(2) A mixture of 3,4-dihydro-1(2H)-naphthalenone (4.5 g) and 4-tert-butylbenzaldehyde (5.0 g) was stirred with a solution of 4% potassium hydroxide in methanol (100 ml) for 64 hours at room temperature. The mixture was neutralised with glacial acetic acid, followed by dilution with water (100 ml). The resulting copious white precipitate was filtered off, washed with water and dried in vacuo to give 2-(4-tert-butylbenzylidene)-3,4-dihydro-1(2H)-naphthalenone.

The following compounds were prepared by methods similar to the above:

2-(4-Bromobenzylidene)-3,4-dihydro-1(2H)-naphthalenone
2-(4-Chlorobenzylidene)-3,4-dihydro-1(2H)-naphthalenone
2-(4-Fluorobenzylidene)-3,4-dihydro-1(2H)-naphthalenone
2-(3,4-Dichlorobenzylidene)-3,4-dihydro-1(2H)-naphthalenone
2-(3,4-Dichlorobenzylidene)-5-methoxy-3,4-dihydro-1(2H)-naphthalenone
2-(3,4-Dichlorobenzylidene)-6-methoxy-3,4-dihydro-1(2H)-naphthalenone
2-(3,4-Dichlorobenzylidene)-7-methoxy-3,4-dihydro-1(2H)-naphthalenone
2-(4-Chloro-3-trifluoromethylbenzylidene)-3,4-dihydro1(2H)-naphthalenone
2-(4-Methoxybenzylidene)-3,4-dihydro-1(2H)-naphthalenone
2-(3,4-Dimethoxybenzylidene)-3,4-dihydro-1(2H)-naphthalenone
2-(3,4-Methylenedioxybenzylidene)-3,4-dihydro-1(2H)-naphthalenone
7-Methoxy-2-(3,4-methylenedioxybenzylidene)-3,4-dihydro-1(2H)-naphthalenone
2-(1,4-Benzodioxan-6-ylidene)-3,4-dihydro-1(2H)-naphthalenone
2-(4-Dimethylaminobenzylidene)-3,4-dihydro-1(2H)-naphthalenone
2-(3,5-Di-tert-butyl-4-hydroxybenzylidene)-3,4-dihydro-1(2H)-naphthalenone
2-(3-Trifluoromethylbenzylidene)-3,4-dihydro-1(2H)-naphthalenone
2-(4-Trifluoromethylbenzylidene)-3,4-dihydro-1(2H)-naphthalenone
2-(4-Nitrobenzylidene)-3,4-dihydro-1(2H)-naphthalenone
5-Methoxy-2-(4-nitrobenzylidene)-3,4-dihydro-1(2H)-naphthalenone
6-Methoxy-2-(4-nitrobenzylidene)-3,4-dihydro-1(2H)-naphthalenone
7-Methoxy-2-(4-nitrobenzylidene)-3,4-dihydro-1(2H)-naphthalenone
2-(4-Methanesulphonylbenzylidene)-3,4-dihydro-1(2H)-naphthalenone
2-(4-Methanesulphonylbenzylidene)-7-methoxy-3,4-dihydro-1(2H)-naphthalenone
2-(4-Methoxycarbonylbenzylidene)-3,4-dihydro-1(2H)-naphthalenone
2-(2-Naphthylidene)-3,4-dihydro-1(2H)-naphthalenone
2-(2-Furfurylidene)-7-methoxy-3,4-dihydro-1(2H)-naphthalenone
2-(2-Thienylidene)-3,4-dihydro-1(2H)-naphthalenone
7-Methoxy-2-(2-thienylidene)-3,4-dihydro-1(2H)-naphthalenone
2-(3-Thienylidene)-3,4-dihydro-1(2H)-naphthalenone
7-Methoxy-2-(3-thienylidene)-3,4-dihydro-1(2H)-naphthalenone
7-Methoxy-2-(3-methyl-2-thienylidene)-3,4-dihydro-1(2H)-naphthalenone
7-Methoxy-2-(5-methoxy-2-thienylidene)-3,4-dihydro-1(2H)-naphthalenone
7-Methoxy-2-(1-methyl-2-pyrrolylmethylene)-3,4-dihydro-1(2H)-naphthalenone
2-(3-Pyridylmethylene)-3,4-dihydro-1(2H)-naphthalenone
7-Methoxy-2-(3-pyridylmethylene)-3,4-dihydro-1(2H)-naphthalenone
7-Methoxy-2-(4-pyridylmethylene)-3,4-dihydro-1(2H)-naphthalenone
2-(Benzo[b]thien-2-ylidene-7-methoxy-3,4-dihydro-1(2H)-naphthalenone
2-(3-Bromobenzylidene)-3,4-dihydro-1(2H)-naphthalenone
2-(3-Chlorobenzylidene)-3,4-dihydro-1(2H)-naphthalenone
2-(3-Fluorobenzylidene)-3,4-dihydro-1(2H)-naphthalenone
2-(3,4-Difluorobenzylidene)-3,4-dihydro-1(2H)-naphthalenone
2-(3-Fluoro-4-methoxybenzylidene)-3,4-dihydro-1(2H)-naphthalenone
2-(3-Chloro-4-methoxybenzylidene)-3,4-dihydro-1(2H)-napthalenone
2-(3-Chloro-4-fluorobenzylidene)-3,4-dihydro-1(2H)-naphthalenone
2-(3-Bromo-4-fluorobenzylidene)-3,4-dihydro-1(2H)-naphthalenone
2-(3-Methoxybenzylidene)-3,4-dihydro-1(2H)-naphthalenone
2-(3-Trifluoromethoxybenzylidene)-3,4-dihydro-1(2H)-naphthalenone
2-[3,5-Bis(trifluoromethyl)benzylidene]-3,4-dihydro-1(2H)-naphthalenone
2-(3-Methoxycarbonylbenzylidene)-3,4-dihydro-1(2H)-naphthalenone
7-Methoxy-2-(3-methoxycarbonylbenzylidene)-3,4-dihydro-(2H)-naphthalenone
7-Methoxy-2-(3-nitrobenzylidene)-3,4-dihydro-1(2H)-naphthalenone

EXAMPLE 2

To a stirred suspension of 2-(3-nitrobenzylidene)-3,4-dihydro-1(2H)-naphthalenone (29.0 g) and malononitrile (10.27 g) in dry dimethylformamide (250 ml) at room temperature was added piperidine (2 ml) dropwise. The mixture turned black and all solid dissolved. After 24 hours, the solution was poured into saturated aqueous sodium chloride solution (1 liter) whereupon a red gummy solid was deposited. The mixture was filtered and the collected gum washed with water and then stirred with methanol for 30 minutes. Filtration and drying in vacuo yielded 2-amino-4-(3-nitrophenyl)-4H-5,6-dihydronaphtho[1,2-b]pyran 3-carbonitrile as a very pale yellow powder, m.p. 175°–176° C.

EXAMPLE 3

To a stirred suspension of 2-(4-trifluoromethylbenzylidene)-3,4-dihydro-1(2H)-naphthalenone (27.0 g) and malononitrile (8.85 g) in dimethylformamide (150 ml) at room temperature was added dropwise piperidine (4 ml). The mixture turned black and all the solid dissolved over a two hour period. After 24 hours, the solution was poured into a 1:1 mixture of water and dichloromethane (1 liter). The organic layer was separated and the aqueous phase extracted further with dichloromethane (2×200 ml). The combined organics were washed with water (2×300 ml), dried (MgSO$_4$), filtered and concentrated in vacuo to yield a brown gum. This was triturated with methanol to yield a solid that was recrystallised from methanol/water yielding 2-amino-4-(4-trifluoromethylphenyl)-4H-5,6-dihydronaphtho [1,2-b]pyran 3-carbonitrile as glistening colourless crystals, m.p. 204°–206° C.

The following compounds were prepared in a manner similar to that described in Examples 2 or 3.

2-Amino-4-(4-bromophenyl)-4H-5,6-dihydronaphtho[1,2-b]pyran 3-carbonitrile, m.p. 178°-179° C.

2-Amino-4-(4-chlorophenyl)-4H-5,6-dihydronaphtho[1,2-b]pyran 3-carbonitrile, m.p. 171°-172° C.

2-Amino-4-(4-fluorophenyl)-4H-5,6-dihydronaphtho[1,2-b]pyran 3-carbonitrile, m.p. 188°-190° C.

2-Amino-4-(3,4-dichlorophenyl)-4H-5,6-dihydronaphtho [1,2-b]pyran 3-carbonitrile, m.p. 215°-216° C.

2-Amino-4-(3,4-dichlorophenyl)-7-methoxy-4H-5,6-dihydronaphtho[1,2-b]pyran 3-carbonitrile, m.p. 216°-217° C.

2-Amino-4-(3,4-dichlorophenyl)-8-methoxy-4H-5,6-dihydronaphtho[1,2-b]pyran 3-carbonitrile, m.p. 199°-200° C.

2-Amino-4-(3,4-dichlorophenyl)-9-methoxy-4H-5,6-dihydronaphtho[1,2-b]pyran 3-carbonitrile, m.p. 200°-201° C.

2-Amino-4-(4-chloro-3-trifluoromethylphenyl)-4H-5,6-dihydronaphtho[1,2-b]pyran 3-carbonitrile, m.p. 204°-206° C.

2-Amino-4-(4-methoxyphenyl)-4H-5,6-dihydronaphtho[1,2-b]pyran 3-carbonitrile, m.p. 177°-178° C.

2-Amino-4-(3,4-dimethoxyphenyl)-4H-5,6-dihydronaphtho[1,2-b]pyran 3-carbonitrile, m.p. 190°-191° C.

2-Amino-4-(3,4-methylenedioxyphenyl)-4H-5,6-dihydronaphtho[1,2-b]pyran 3-carbonitrile, m.p. 250°-252° C.

2-Amino-9-methoxy-4-(3,4-methylenedioxyphenyl)-4H-5,6-dihydronaphtho[1,2-b]pyran 3-carbonitrile, m.p. 185°-186° C.

2-Amino-4-(1,4-benzodioxan-6-yl)-4H-5,6-dihydronaphtho[1,2-b]pyran 3-carbonitrile, m.p. 203°-204° C.

2-Amino-4-(4-dimethylaminophenyl)-4H-5,6-dihydronaphtho[1,2-b]pyran 3-carbonitrile, m.p. 201°-202° C.

2-Amino-4-(3,5-di-tert-butyl-4-hydroxyphenyl)-4H-5,6-dihydronaphtho[1,2-b]pyran 3-carbonitrile, m.p. 222°-224° C.

2-Amino-4-(4-tert-butylphenyl)-4H-5,6-dihydronaphtho[1,2-b]pyran 3-carbonitrile, m.p. 194°-195° C.

2-Amino-4-(3-trifluoromethylphenyl)-4H-5,6-dihydronaphtho[1,2-b]pyran 3-carbonitrile, m.p. 195.5°-196° C.

2-Amino-4-(4-nitrophenyl)-4H-5,6-dihydronaphtho[1,2-b]pyran 3-carbonitrile, m.p. 213°-214° C.

2-Amino-7-methoxy-4-(4-nitrophenyl)-4H-5,6-dihydronaphtho[1,2-b]pyran 3-carbonitrile, m.p. 194°-195° C.

2-Amino-8-methoxy-4-(4-nitrophenyl)-4H-5,6-dihydronaphtho[1,2-b]pyran 3-carbonitrile, m.p. 166°-167° C.

2-Amino-9-methoxy-4-(4-nitrophenyl)-4H-5,6-dihydronaphtho[1,2-b]pyran 3-carbonitrile, m.p. 185°-186° C.

2-Amino-4-(4-methanesulphonylphenyl)-4H-5,6-dihydronaphtho[1,2-b]pyran 3-carbonitrile, m.p. 196°-197° C.

2-Amino-4-(4-methanesulphonylphenyl)-9-methoxy-4H-5,6-dihydronaphtho[1,2-b]pyran 3-carbonitrile, m.p. 188°-189° C.

Methyl-4-(2-Amino-3-cyano-4H-5,6-dihydronaphth[1,2-b]pyran-4-yl)benzoate, m.p. 189°-190° C.

2-Amino-4-(2-naphthyl)-4H-5,6-dihydronaphtho[1,2-b]pyran 3-carbonitrile, m.p. 185°-186° C.

2-Amino-4-(2-furyl)-9-methoxy-4H-5,6-dihydronaphtho[1,2-b]pyran 3-carbonitrile, m.p. 148°-149° C.

2-Amino-4-(2-thienyl)-4H-5,6-dihydronaphtho[1,2-b]pyran 3-carbonitrile, m.p. 170°-171° C.

2-Amino-4-(3-thienyl)-4H-5,6-dihydronaphtho[1,2-b]pyran 3-carbonitrile, m.p. 158°-159° C.

2-Amino-9-methoxy-4-(2-thienyl)-4H-5,6-dihydronaphtho[1,2-b]pyran 3-carbonitrile, m.p. 198°-199° C.

2-Amino-9-methoxy-4-(3-thienyl)-4H-5,6-dihydronaphtho[1,2-b]pyran 3-carbonitrile, m.p. 160°-161° C.

2-Amino-9-methoxy-4-(3-methyl 2-thienyl)-4H-5,6-dihydronaphtho[1,2-b]pyran 3-carbonitrile, m.p. 179°-180° C.

2-Amino-9-methoxy-4-(5-methoxy 2-thienyl)-4H-5,6-dihydronaphtho[1,2-b]pyran 3-carbonitrile, m.p. 130°-131° C.

2-Amino-9-methoxy-4-(1-methyl 2-pyrrolyl)-4H-5,6-dihydronaphtho[1,2-b]pyran 3-carbonitrile, m.p. 190°-191° C.

2-Amino-4-(3-pyridyl)-4H-5,6-dihydronaphtho[1,2-b]pyran 3-carbonitrile, m.p. 165°-166° C.

2-Amino-9-methoxy-4-(3-pyridyl)-4H-5,6-dihydronaphtho[1,2-b]pyran 3-carbonitrile, m.p. 230°-232° C.

2-Amino-9-methoxy-4-(4-pyridyl)-4H-5,6-dihydronaphtho[1,2-b]pyran 3-carbonitrile, m.p. 205°-207° C.

2-Amino-4-(benzo[b]thiophen-2-yl)-9-methoxy-4H-5,6-dihydronaphtho[1,2-b]pyran 3-carbonitrile, m.p. 214°-215° C.

2-Amino-4-(3-bromophenyl)-4H-5,6-dihydronaphtho[1,2-b]pyran 3-carbonitrile, m.p. 176°-177° C.

(2-Amino-4-(3-chlorophenyl)-4H-5,6-dihydronaphtho[1,2-b]pyran 3-carbonitrile, m.p. 175°-176° C.

2-Amino-4-(3-fluorophenyl)-4H-5,6-dihydronaphtho[1,2-b]pyran 3-carbonitrile, m.p. 169°-170° C.

2-Amino-4-(3,4-difluorophenyl)-4H-5,6-dihydronaphtho[1,2-b]pyran 3-carbonitrile, m.p. 168°-170° C.

2-Amino-4-(3-fluoro-4-methoxyphenyl)-4H-5,6-dihydronaphtho[1,2-b]pyran 3-carbonitrile, m.p. 219°-222° C.

2-Amino-4-(3-chloro-4-methoxyphenyl)-4H-5,6-dihydronapho[1,2-b]pyran 3-carbonitrile, m.p. 203° C.

2-Amino-4-(3-chloro-4-fluorophenyl)-4H-5,6-dihydronaphtho[1,2-b]pyran 3-carbonitrile, m.p. 184°-185° C.

2-Amino-4-(3-bromo-4-fluorophenyl)-4H-5,6-dihydronaphtho[1,2-b]pyran 3-carbonitrile, m.p. 185°-187° C.

2-Amino-4-(3-methoxyphenyl)-4H-5,6-dihydronaphtho[1,2-b]pyran 3-carbonitrile, m.p. 204°-206° C.

2-Amino -4-(3-trifluoromethoxyphenyl)-4H-5,6-dihydronaphtho[1,2-b]pyran 3-carbonitrile, m.p. 141°-143° C.

2-Amino-4-[3,5-bis(trifluoromethyl)phenyl]-4H-5,6-dihydronaphtho[1,2-b]pyran 3-carbonitrile, m.p. 228°-231° C.

2-Amino-9-methoxy-4-(3-nitrophenyl)-4H-5,6-dihydronaphtho[1,2-b]pyran 3-carbonitrile, m.p. 192°-194° C.

Methyl 3-(2-amino-3-cyano-4H-5,6-dihydronaphtho[1,2-b]pyran-4-yl) benzoate, m.p. 217°-218° C.

Methyl 3-(2-amino-3-cyano-9-methoxy-4H-5,6-dihydronaphtho[1,2-b]pyran-4-yl) benzoate, m.p. 159°-160° C.

EXAMPLE 4

To a stirred ice-cooled solution of 2-amino-4-(3-nitrophenyl)-4H-5,6-dihydronaphtho [1,2-b]pyran 3-carbonitrile (12.05 g) and dry pyridine (18 ml) in dry dimethylformamide (200 ml) was added dropwise over 15 minutes acetyl chloride (16 ml). A heavy white precipitate appeared. The ice bath was removed and the stirred at room temperature for 65 hours during which time all the solid dissolved and the solution had turned black. This was poured into saturated aqueous sodium chloride solution (300 ml) and the product extracted with dichloromethane (2×250 ml). The combined extracts were washed with saturated aqueous copper sulphate solution (4×200 ml), water (2×200 ml), saturated aqueous sodium chloride solution (2×200 ml) and dried (MgSG$_4$). Filtration followed by concentration in vacuo yielded a viscous red gum (16.5 g). This was dissolved in dichloromethane and passed through a pad of neutral alumina eluting with ether/dichloromethane (1:1). Combination and concentration of appropriate fractions yielded a crisp yellow solid (12.0 g). This was redissolved in dichloromethane (100 ml) and stirred with neutral alumina (50 g) for 16 hours. The alumina was filtered off, washed well with dichloromethane and the resulting solution concentrated yielding a crisp bright yellow solid (9.64 g) that was recrystallised from methanol yielding 2-acetylamino-4-(3-nitrophenyl)-4H-5,6-dihydronaphtho[1,2-b]pyran 3-carbonitrile as a pale yellow powdery solid, m.p. 219°-221° C.

The following compounds were prepared in a similar manner:

2-Acetylamino-4-(4-nitrophenyl)-4H-5,6-dihydronaphtho[1,2-b b]pyran 3-carbonitrile, m.p. 231°-234° C.

2-Acetylamino-4-(3-trifluoromethylphenyl)-4H-5,6-dihydronaphtho[1,2-b]pyran 3-carbonitrile, m.p. 177°-179° C.

2-Acetylamino-4-(4-chlorophenyl)-4H-5,6-dihydronaphtho[1,2-b]pyran 3-carbonitrile, m.p. 219°-223° C.

2-Acetylamino-4-(4-fluorophenyl)-4H-5,6-dihydronaphtho[1,2-b]pyran 3-carbonitrile, m.p. 203°-208° C.

2-Acetylamino-4-(2-thienyl)-4H-5,6-dihydronaphtho[1,2-b]pyran 3-carbonitrile, m.p. 235°-237° C.

2-Acetylamino-9-methoxy-4-(3-thienyl)-4H-5,6-dihydronaphtho[1,2-b]pyran 3-carbonitrile, m.p. 197°-198° C.

2-Acetylamino-4-(3,4-dimethoxyphenyl)-4H-5,6-dihydronaphtho[1,2-b]pyran 3-carbonitrile, m.p. 178°-180° C.

2-Acetylamino-4-(3,4-dichlorophenyl)-4H-5,6-dihydronaphtho[1,2-b]pyran 3-carbonitrile, m.p. 196°-198° C.

2-Acetylamino-4-(3-pyridyl)-4H-5,6-dihydronaphtho[1,2-b]pyran 3-carbonitrile, m.p. 205°-207° C.

2-Acetylamino-9-methoxy-4-(2-thienyl)-4H-5,6-dihydronaphtho[1,2-b]pyran 3-carbonitrile, m.p. 202°-204° C.

Methyl 3-[2-(N-acetylamino)-3-cyano-4H-5,6-dihydronaphtho[1,2-b]pyran-4-yl] benzoate, m.p. 220°-225° C.

Methyl 3-[2-(N-acetylamino)-3-cyano-9-methoxy-4H-5,6-dihydronaphtho[1,2-b]pyran-4-yl] benzoate, m.p. 90°-91° C.

EXAMPLE 5

To a stirred suspension of sodium hydride (60% dispersion in oil, 0.39 g) in dry dimethylformamide (80 ml) at −5° C. under nitrogen was added dropwise during 10 minutes a solution of 2-acetylamino-4-(3-nitrophenyl)-4H-5,6-dihydronaphtho[1,2-6]pyran 3-carbonitrile (2.80 g) in dry dimethylformamide (20 ml). The mixture rapidly turned orange and there was a weak exotherm. After stirring at −5° C. for 50 minutes, methyl iodide (1.42 g) was added dropwise. The cooling bath was removed and stirring continued at room temperature for 4 hours. The mixture was then poured into water (200 ml) and the product extracted into dichloromethane (2×100 ml). The combined organic extracts were washed with water (3×50 ml), dried (Na$_2$SO$_4$), filtered and evaporated in vacuo yielding a crisp yellow solid. This was dissolved in dichloromethane and passed through a short column of neutral alumina eluting with dichloromethane/ether (1:1). Combination and evaporation in vacuo of appropriate fractions yielded 2-(N-acetyl-N-methylamino)-4-(3-nitrophenyl)-4H-5,6-dihydronaphtho[1,2-b]pyran 3-carbonitrile as a pale yellow powder, m.p. 154°-155° C.

The following compounds were prepared in a similar manner:

2-(N-acetyl-N-methylamino)-9-methoxy-4-(3-thienyl)-4H-5,6-dihydronaphtho[1,2-b]pyran 3-carbonitrile, m.p. 181°-182° C.

Methyl 3-[2-(N-acetyl-N-methylamino)-3-cyano-4H-5,6-dihydronaphtho[1,2-b]pyran-4-yl] benzoate, m.p. 137°-138° C.

Methyl 3-[2-N-acetyl-N-methylamino)-3-cyano-9-methoxy-4H-5,6-dihydronaphtho[1,2-b]pyran-4-yl] benzoate, m.p. 140°-141° C.

EXAMPLE 6

A mixture of 2-amino-4-(3-nitrophenyl)-4H-5,6-dihydronaphtho[1,2-b]pyran 3-carbonitrile (2.50 g) and triethyl orthoformate (25 ml) was heated under reflux for six hours. The cooled solution was concentrated in vacuo and the residual yellow/brown solid stirred with methanol for 30 minutes. Undissolved solid was filtered off, taken up in chloroform, chromatographed on silica gel with chloroform as eluant yielding 1.6 g of crude product. This recrystallised from ethanol yielding 2-(E)-(ethoxymethyleneamino)-4-(3-nitrophenyl)-4H-5,6-dihydronaphtho[1,2-b]pyran-3-carbonitrile as glistening pale yellow needles, m.p. 168°-171° C.

The following compounds were pre;pared in a similar manner:

4-(3,4-Dimethoxyphenyl)-2-(E)-ethoxymethyleneamino-4H -5,6-dihydronaphtho[1,2-b]pyran 3-carbonitrile, m.p. 86°-88° C.

2-(E)-Ethoxymethyleneamino-9-methoxy-4-(2-thienyl)-4H-5,6-dihydronaphtho[1,2-b]pyran 3-carbonitrile, m.p. 132°-134° C.

4-(3,4-Dichlorophenyl)-2-(E)-ethoxymethyleneamino-4H-5,6-dihydronaphtho[1,2-b]pyran 3-carbonitrile, m.p. 156°-158° C.

2-(E)-Ethoxymethyleneamino-4-(3-pyridyl)-4H-5,6-dihydronaphtho[1,2-b]pyran 3-carbonitrile, m.p. 130°-132° C.

EXAMPLE 7

2-Amino-9-methoxy-4-(2-thienyl)-4H-5,6-dihydronaphtho[1,2-b]pyran 3-carbonitrile (0.5 g) was dissolved in tetrahydrofuran (20 ml) and treated with pyridine (0.47 g) and then succinyl chloride (0.69 g), generating a cream suspension. This was brought to reflux. After a few hours, more pyridine (0.23 g) was added. After 12 hours at reflux, the reaction mixture was allowed to cool and quenched with water. This mixture was diluted with chloroform and the two phase mixture passed through a pad of celite. The chloroform layer was separated, washed with brine and dried ($MgSO_4$). This solution was passed quickly through a small pad of silica and the resulting solution concentrated. Trituration of the residue with ethyl acetate plus a little hexane yielded 9-methoxy-2-(N-succinimido)-4-(2-thienyl)-4H-5,6-dihydronaphtho[1,2-b]pyran 3-carbonitrile as a brown solid (m.p. 234°-236° C.).

The following compounds were prepared in a similar manner:

4-(3,4-Dimethoxyphenyl)-2-(N-succinimido)-4H-5,6-dihydronaphtho[1,2-b]pyran 3-carbonitrile, m.p. 220°-222° C.

4-(3,4-Dichlorophenyl)-2-(N-succinimido)-4H-5,6-dihydronaphtho[1,2-b]pyran 3%carbonitrile, m.p. 215°-217° C.

4-(3-Nitrophenyl)-2-(N-succinimido)-4H-5,6-dihydronaphtho[1,2-b]pyran 3-carbonitrile, m.p. 96°-98° C.

EXAMPLE 8

2-(E)-Ethoxymethyleneamino-4-(3-nitrophenyl)-4H-5,6-dihydronaphtho[1,2-b]pyran 3-carbonitrile (0.5 g) and 2-aminopyridine (0.23 g) were dissolved in tetrahydrofuran (20 ml) and the solution heated at reflux under nitrogen overnight. Two further equivalents of 2-aminopyridine were then added and heating continued for a further 24 hours. By this time a precipitate had formed. This was collected by filtration and washed twice with warm tetrahydrofuran, yielding 1-(2-pyridyl)-3-[4-(3-nitrophenyl)-3-cyano-4H-5,6-dihydronaphtho[1,2-b]pyran-2-yl]formamidine, m.p. 223°-225° C.

As previously indicated these compounds are useful for the treatment of diabetic complications. The activity of the compounds of the present invention was identified through in vitro studies using activated endothelial cells.

Retinal capillary endothelial cell cultures were initiated from bovine eyes using a modification of the procedure of Buzney et al., *Investigative Ophthalmology and Visual Sciences,* 24: 470–480 (1983). Bovine eyes were transported on ice from a local abattoir. Extraocular muscle was trimmed from the eye, and the eye bisected posterior to the ora serrata. The vitreous and anterior portion of the eye were discarded, and the neuro-retina was gently dissected from the posterior eyecup. The retinas from 20 cattle were pooled and homogenized (5 strokes of a Teflon/glass homogenizer) in Hank's saline. The homogenate was passed through a 350μ filter to remove large debris and a 210μ filter to remove large vessels. The microvessels were trapped on a 85μ filter. The microvessels were resuspended in Hank's saline and digested with 7.5 mg/ml bacterial collagenase (Boeringher Mannheim, Indianapolis) in Hank's saline for 1 hour at 37° C. The cells were pelleted by centrifugation (100×g, 10 min), resuspended in 5 ml Endothelial Growth Media (EGM, Clonetics) and seeded in a gelatin-coated T-25 flask. After 24 hours the cells were trypsinized and replated in a gelatin coated T225. At 7 days and again at 14 days the cultures were labeled with acetylated lipoproteins labeled with the fluorescent probe (1,1'-dioctadecyl-3,3,3,3,-tetramethyl-indocarbocyanine perchlorate). The endothelial cells were separated from contaminating cell types using a fluorescent cell sorter as described in Voyta et al., *J. Cell Biology.* 99: 2034–2040 (1984).

Retinal capillary endothelial cells were seeded into 96-well plates and grown to confluence ($10^5$ cells/well) in EGM containing 10% fetal bovine serum (FBS). The media was changed to Dubecco's Modified Eagle's Medium with 10% fetal bovine serum 24 hours prior to the assay. The cells were treated with 50 nM 4-b phorbol 12,13-dibutyrate (4-b PDBu) to activate PKC and produce the activated endothelial phenotype characteristic of the diabetic state. The activated cells were treated with a series of dilutions of the test compounds. The phorbol esters and the test compounds were dissolved in DMSO before adding to the culture media. The cultures were incubated at 37° C. for 48 hours. Following treatment, the cells were lysed with 25 mM $NH_4OH$ in 0.5% triton X-100.

The activation of bovine retinal capillary endothelial cells was monitored through alterations in cellular plasminogen activator (PA) activity in the cell lysates. Plasminogen activator activitq was determined in a 50 μl aliquot of cell lysate using the synthetic substrate H-D-valyl-L-leucyl-lysine-p-nitroaniline dihydrochloride (Kabi).

Treatment of confluent bovine retinal capillary endothelial cells for 48 hours with PDBu resulted in a 12 fold increase in PA activity associated with the cell layer and a 12 fold increase in PA released into the media. There was also a two fold increase in cell number. This increase in activation occurred only after treatment with phorbol esters known to activate PKC (4-b PDBu, 4-b PMA, but not 4-a PDBu, 4-a PMA). No cleavage of the synthetic substrate was observed when plasminogen was omitted from the assay mixture, indicating that the increase in activity observed in phorbol treated cultures was restricted to activators of plasminogen. Dose-response curves generated for 4-b PDBu and 4-b PMA indicated $IC_{50}$s of 50 nM and 5 nM respectively. Elevated PA activity was observed only after prolonged (at least 8 hours) stimulation with phorbol esters. The PA activity continued to increase in a time and dose dependent manner for up to 72 hours, but constant stimulation with phorbol ester was required to maintain endothelial cell activation. Removal of the phorbol ester resulted in a rapid return of PA activity to normal levels.

Cell toxicity was determined in a parallel series of cultures using a neutral red assay. Borenfreund, E. and Puerner, J, *J. Tiss. Cult. Meth.* 9: 7 (1984). The effectiveness of the present compounds to inhibit endothelial cell activation was found to be distinct from cell toxicity. In general, the compounds of the present invention were shown to be effective in inhibiting the endothelial cell activation induced by phorbol esters and have a PA $IC_{50}$ value in this test below 10 μM. The in vitro endothelial cell model was correlated with in situ and in vivo activities by the following models.

The granulation tissue chamber model evaluates in situ the compound's ability to block the increase in blood flow and permeability induced by high glucose. In this model, circles of skin and removed from the backs of normal rats and stainless steel screw-cap chambers are mounted. New granulation tissue is formed within the chambers. Addition of 30–35 mM glucose (0.5 ml) twice daily to the chambers for 7 days induced a vascular dysfunction similar to that of diabetes-that is there is an increase in blood vessel permeability and an increase in blood flow. Blood flow is measured through the use of radiolabeled microspheres, and permeability is quantified using a dual label technique with iodinated albumin ($^{125}I/^{131}I$). Details of the model can be found in Tilton, et al., *Diabetes* 38: 1258–1270 (1989), and Williamson, et al., *J. Clin. Invest.* 85: 1167–1172 (1990). Representative compounds are dissolved in DMSO and diluted in a balanced salt solution to achieve a final concentration of 20 or 50 µM. The granulation chamber tissue is treated twice daily for 7 days to determine their effects on glucose-induced vascular dysfunction. Addition of 30–35 mM glucose to the granulation chamber induced a vascular dysfunction characterized by increased vessel permeability and increased blood flow.

The steptozotocin-induced diabetic rat model evaluates in vivo the compounds ability to block the microvascular dysfunction associated with streptozotocin-induced diabetes. Rats are made diabetic with an injection of streptozotocin, and the rats are feed ad libitum with a diet containing 0.1% of a representative compound. Blood flow is measured through the use of radiolabeled microspheres while permeability is quantified using a dual label technique with iodinated albumin ($^{125}I/^{131}I$). Details of the model can be found in Tilton et al., *Diabetes* 38: 1258–1270 (1989), and Williamson et al., *J. Clin. Invest.* 85: 1167–1172 (1990).

The compounds may be administered by various routes, for example, by the oral or rectal route, topically or parenterally, for example by injection, being usually employed in the form of a pharmaceutical composition. Such compositions are prepared in a manner well known in the pharmaceutical art and normally comprise at least one active compound in association with a pharmaceutically-acceptable diluent or carrier. In making the compositions, the active ingredient will usually be mixed with a carrier, or diluted by a carrier, and/or enclosed with a carrier which may, for example, be in the form of a capsule, sachet, paper or other container. Where the carrier serves as a diluent, it may be solid, semi-solid, or liquid material which acts as a vehicle, excipient or medium for the active ingredient. Thus, the composition may be in the form of tablets, lozenges, sachets, cachets, elixirs, suspensions, as a solid or in a liquid medium, ointments containing, for example, up to 10% by weight of the active compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propylhydroxybenzoate, talc magnesium stearate and mineral oil.

The compositions of the injection may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg, for example, from 25 mg to 200 mg. The term 'unit dosage form' refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the therapeutic dosage administered will be determined by the physician in the light of the relevant circumstances including the condition to be treated, the choice of compound to be administered and the chosen route of administration, and therefore the above dosage ranges are not intended to limit the scope of the invention in any way.

The term "treating" includes the administration of a compound of the present invention to prevent the onset of the symptoms, alleviating the symptoms, or eliminating the disease, condition or disorder.

We claim:

1. A method of treating diabetic complications, which comprises administering to a patient in need of treatment a therapeutic dosage of a compound of the Formula (I):

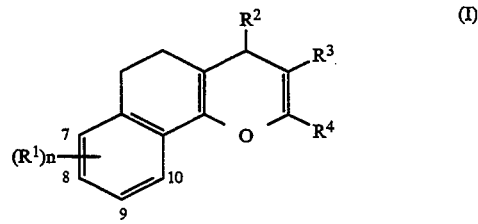

wherein n is 0, 1 or 2;

R$^1$ is C$_1$–C$_4$ alkoxy, OH, or COOH attached at any of the positions 7, 8, 9, or 10;

R$^2$ is phenyl, naphthyl or heteroaryl selected from thienyl, pyrrolyl, pyridyl, and benzothienyl;

said phenyl being optionally substituted in position 3, 4, or 5 with one or two substituents being selected from halo, C$_{1-4}$ alkoxy, nitro, or when the substitution is in position 3, trifluoromethyl, carboxy, trifluoromethoxy or COOR$^{15}$ where R$^{15}$ is an ester group;

said naphthyl and heteroaryl being optionally substituted at any available position with one substituent selected from halo, C$_{1-4}$ alkyl, C$_{1-4}$ alkoxy, hydroxy, or trifluoromethyl;

or R$^2$ is furanyl optionally substituted with C$_{1-4}$ alkyl;

R$^3$ is nitrile; and

R$^4$ is —NR$^{11}$R$^{12}$, —NR$^{11}$COR$^{12}$, or —N=CHOCH$_2$R$^{11}$ where R$^{11}$ and R$^{12}$ are each hydrogen or C$_{1-4}$ alkyl.

2. A method of claim 1 wherein R$^2$ is 2-furanyl or substituted phenyl.

3. A method of claim 2 wherein R$^4$ is —NR$^{11}$R$^{12}$ and R$^{11}$ and R$^{12}$ are each hydrogen.

4. A method of claim 3 wherein R$^2$ is substituted phenyl.

5. A method of inhibiting endothelial cell activation, which comprises administering to a patient in need of treatment a therapeutic dosage of a compound of the Formula I:

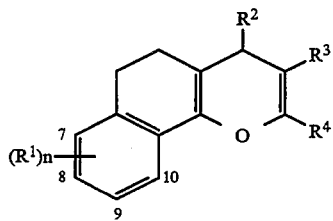

(I)

wherein n is 0, 1 or 2;
- $R^1$ is $C_1$-$C_4$ alkoxy, OH, or COOH attached at any of the positions 7, 8, 9, or 10;
- $R^2$ is phenyl, naphthyl or heteroaryl selected from thienyl, pyrrolyl, pyridyl, and benzothienyl; said phenyl being optionally substituted in positions 3, 4 or 5 with one or two substituents selected from halo, $C_{1-4}$alkoxy, nitro, or when the substitution is in position 3, trifluoromethyl, carboxy, trifluoromethoxy or $COOR^{15}$ where $R^{15}$ is an ester group;
  said naphthyl and heteroaryl being optionally substituted at any available position with one substituent selected from halo, $C_{1-4}$alkyl, $C_{1-4}$alkoxy, hydroxy or trifluoromethyl; or $R^2$ is furanyl optionally substituted with $C_{1-4}$ alkyl;
- $R^3$ is nitrile; and
- $R^4$ is —$NR^{11}R^{12}$, —$NR^{11}COR^{12}$, or —N=CHCH$_2R^{11}$ where $R^{11}$ and $R^{12}$ are each hydrogen or $C_{1-4}$ alkyl.

6. A method of claim 5 wherein $R^2$ is 2-furanyl or substituted phenyl.

7. A method of claim 6 wherein $R^4$ is —$NR^{11}R^{12}$ and $R^{11}$ and $R^{12}$ are each hydrogen.

8. A method of treating vascular dysfunction, which comprises administering to a patient in need of treatment a therapeutic dosage of a compound of the Formula I:

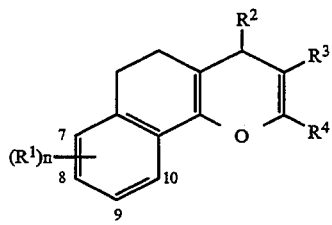

(I)

wherein n is 0, 1 or 2;
- $R^1$ is $C_1$-$C_4$ alkoxy, OH, or COOH attached at any of the positions 7, 8, 9, or 10;
- $R^2$ is phenyl, naphthyl or heteroaryl selected from thienyl, pyrrolyl, pyridyl, and benzothienyl; said phenyl being optionally substituted in positions 3, 4 or 5 with one or two substituents selected from halo, $C_{1-4}$alkoxy, nitro, or when the substitution is in position 3, trifluoromethyl, carboxy, trifluoromethoxy or $COOR^{15}$ where $R^{15}$ is an ester group;
  said naphthyl and heteroaryl being optionally substituted at any available position with one substituent selected from halo, $C_{1-4}$alkyl, $C_{1-4}$alkoxy, hydroxy or trifluoromethyl; or $R^2$ is furanyl optionally substituted with $C_{1-4}$ alkyl;
- $R^3$ is nitrile; and
- $R^4$ is —$NR^{11}R^{12}$, —$NR^{11}COR^{12}$, or —N=CHCH$_2R^{11}$ where $R^{11}$ and $R^{12}$ are each hydrogen or $C_{1-4}$ alkyl.

9. A method of claim 8 wherein $R^2$ is 2-furanyl or substituted phenyl.

10. A method of claim 9 wherein $R^4$ is —$NR^{11}R^{12}$ and $R^{11}$ and $R^{12}$ are each hydrogen.

* * * * *

UNITED STATES PATENT AND TRADEMARK OFFICE
CERTIFICATE OF CORRECTION

PATENT NO. : 5,378,717

DATED : January 3, 1995

INVENTOR(S) : Michael Brunavs, et al.

It is certified that error appears in the above-identified patent and that said Letters Patent is hereby corrected as shown below:

Column 1, line 32, please replace the word "prostrornelysin" with the word -- prostromelysin--.

Column 3, line 41, please replace the word "sales," with the word -- salts,--.

Column 4, line 39, please replace the word "acylazed" with the word -- acylated --.

Column 6, line 21, please replace the phrase "2-(3-Bromo -4-fluorobenzylidene)-3,4-dihydro" with the following phrase --2-(3-Bromo-4-fluorobenzylidene)-3,4-dihydro --.

Column 7, line 66, please replace the phrase "Methyl-4-(2-Amino-3-cyano-4H -5,6-dihy-" with the following phrase "Methyl-4-(2-Amino-3-cyano-4H-5,6-dihy- --.

Column 11, line 26, please replace the phrase "dihydronaphthol[1,2-b]pyran 3%carbonitrile, m.p." with the following phrase __dihydronaphtho[1,2-b]pyran 3-

Signed and Sealed this

Twenty-seventh Day of July, 1999

Attest:

Attesting Officer

Q. TODD DICKINSON

Acting Commissioner of Patents and Trademarks